US005723695A

United States Patent [19]

Wevers et al.

[11] Patent Number: 5,723,695
[45] Date of Patent: Mar. 3, 1998

[54] CONTINUOUS PROCESS FOR THE MANUFACTURE OF SODIUM $C_4$-$C_8$ALKOXIDE

[75] Inventors: Jan Hendrik Wevers, Mainz-Kastel; Robert Jan Hendrik Scheffer, Ingelheim, both of Germany

[73] Assignee: American Cyanamid Company, Madison, N.J.

[21] Appl. No.: 459,059

[22] Filed: Jun. 2, 1995

[51] Int. Cl.$^6$ ............................................. C07C 31/30
[52] U.S. Cl. ............................................................ 568/851
[58] Field of Search .................................................. 568/851

[56] References Cited

U.S. PATENT DOCUMENTS 4,150,244  4/1979  Knorre et al. ............................ 568/851

FOREIGN PATENT DOCUMENTS

| 252637 | 5/1988 | Czech Rep. . |
| 070719 | 12/1977 | Japan . |
| 52-153904 | 12/1977 | Japan . |
| 53-23908 | 3/1978 | Japan . |

*Primary Examiner*—Gary Geist
*Assistant Examiner*—Rosalynd Keys
*Attorney, Agent, or Firm*—Charles F. Costello, Jr.

[57] ABSTRACT

There is provided a safe, efficient process for the production of sodium $C_4$–$C_8$alkoxide which utilizes a less than stoichiometric quantity of a $C_4$–$C_8$alcohol and the option of a continuous recycle of the unreacted sodium metal.

24 Claims, No Drawings

CONTINUOUS PROCESS FOR THE MANUFACTURE OF SODIUM $C_4$-$C_8$ALKOXIDE

BACKGROUND OF THE INVENTION

Sodium $C_4$–$C_8$alkoxides are important, versatile chemicals useful in a wide variety of synthetic reactions and manufacturing procedures wherein a strong organic base is desired. Although the formation of a sodium $C_4$–$C_8$alkoxide by the reaction of sodium metal and a $C_4$–$C_8$ alkanol is well-known, in actual practice, the reaction on a large scale may be hazardous and costly. In many processes, the addition of a catalyst is required or energy-intensive reaction conditions, such as high temperature (>160° C.) and high pressure, are required.

Therefore, it is an object of this invention to provide a safe, efficient process for the production of sodium $C_4$–$C_8$alkoxide.

It is another object of this invention to provide a continuous, integrated source of sodium $C_4$–$C_8$alkoxide, suitable for use in a manufacturing process wherein a strong organic base is required.

It is a further object of this invention to provide a ready and convenient source of essentially pure crystalline sodium $C_4$–$C_8$alkoxide suitable for storage and shipping.

It is a feature of this invention that essentially quantitative conversion of the $C_4$–$C_8$alkanol is obtained.

It is an advantage of this invention that by continuous recycle and essentially complete conversion of the reactants, the process is effective with little or no negative environmental impact.

Further objects and features of the invention will become apparent by the detailed description set forth hereinbelow.

SUMMARY OF THE INVENTION

The present invention provides a safe, efficient and essentially quantitative process for the manufacture of sodium $C_4$–$C_8$alkoxide which comprises treating a stirred dispersion of sodium metal in a solvent optionally under an inert atmosphere with a less than stoichiometric amount of a $C_4$–$C_8$alkanol at a temperature of about 110°–140° C. to form a two phase mixture and separating the top phase to obtain the product sodium $C_4$–$C_8$alkoxide as a solvent solution, optionally continuously recycling the remaining phase mixture.

The sodium $C_4$–$C_8$alkoxide solution, thus obtained, may be used as a manufacturing intermediate and directly integrated into an existing manufacturing process stream or, alternatively, the solution may be cooled and filtered to give a pure crystalline sodium $C_4$–$C_8$alkoxide product suitable for storage and shipping.

DETAILED DESCRIPTION OF THE INVENTION

The production and handling of sodium $C_4$–$C_8$alkoxides are frequently costly and hazardous, particularly sodium tertiary-alkoxides, such as sodium t-butoxide. Even so, such strong organic bases are commonly used in synthetic reactions and manufacturing processes.

It has now been found that sodium $C_4$–$C_8$alkoxide may be prepared safely and effectively on a large manufacturing scale with essentially quantitative conversion of the $C_4$–$C_8$ alkanol and optionally the continuous recycle of the unreacted sodium metal. Accordingly, sodium metal is dispersed in a solvent, preferably an aromatic hydro-carbon or mixture thereof having a boiling point greater than 100° C., optionally under an inert atmosphere, at about 100° to 140° C., preferably about 120° to 130° C. A less than stoichiometric amount of a $C_4$–$C_8$alkanol, preferably about 0.1 to 0.9 molar equivalents, more preferably about 0.4 to 0.6 molar equivalents, alone or in combination with a solvent, preferably an aromatic hydrocarbon or mixture thereof, is added to the heated dispersion with rapid stirring to form a two phase reaction mixture. Said reaction mixture is held without stirring at about 100° to 140° C., preferably at about 120° to 130° C., until the phase separation is complete. The top phase is removed by decantation to give a solvent solution of the product sodium $C_4$–$C_8$alkoxide. Optionally, the remaining phase mixture may be cooled to room temperature, treated with additional sodium metal and solvent, heated to about 100° to 140°, preferably 120° to 130° C., optionally under an inert atmosphere with rapid stirring to form a dispersion and treated with a less than stoichiometric amount of a $C_4$–$C_8$ alkanol as described hereinabove to produce a solvent solution of the product sodium $C_4$–$C_8$alkoxide and a phase mixture containing unreacted sodium metal. Said solvent solution of sodium $C_4$–$C_8$alkoxide may be removed by decantation and said phase mixture containing unreacted sodium may be continuously recycled in the above manner. The inventive process is illustrated in Flow Diagram I wherein x and y are molar equivalents of Na and $C_4$–$C_8$ alcohol, respectively, and y<x.

Flow Diagram I

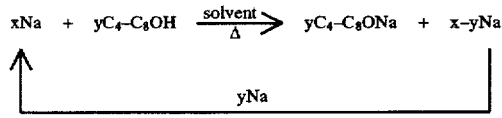

Since y is always less than x, i.e. less than a stoichiometric amount, the starting $C_4$–$C_8$alkanol is essentially quantitatively converted to the product sodium $C_4$–$C_8$alkoxide. Further, since the unreacted sodium is continuously recycled, the inventive process is essentially waste free and, therefore, highly environmentally desirable. Moreover, the inventive process allows for relatively mild reaction conditions, atmospheric pressure, lower reaction temperatures and shorter reaction times which result in high throughput and high productivity without the loss of safety or the burden of hazardous or toxic waste.

Among solvents suitable for use in the process of the invention are aromatic hydrocarbons or mixtures thereof having a boiling point greater than about 100° C., such as xylene, toluene, xylidene, cumene or the like, either alone or in combination.

All $C_4$–$C_8$alkanols are suitable for use in the process of the invention, particularly branched alkanols such as t-butanol or t-amyl alcohol, more particularly t-butanol.

Although the inventive process may be carried out in the presence of air, the introduction of an inert atmosphere such as nitrogen, helium, argon or the like, preferably nitrogen, greatly enhances the safe handling of the hydrogen gas which is produced during the reaction.

In one embodiment of the invention, the product sodium $C_4$–$C_8$alkoxide solvent solution may be integrated directly into an existing manufacturing process stream, such that a continuous production of a solvent solution of a strong organic base is supplied to a manufacturing scale reaction such as a base condensation or Knoevenagel reaction.

In another embodiment of the invention, the product sodium $C_4$–$C_8$ alkoxide solvent solution may be cooled and filtered to give an essentially pure crystalline sodium $C_4$–$C_8$ alkoxide product suitable for storage and shipping and as a resource for a high quality, reagent grade, organic base.

For a more clear understanding of the invention, specific examples are set forth below. These examples are merely illustrative and are not to be understood as limiting the scope and underlying principles of the invention in any way. Indeed, various modifications of the invention, in addition to those shown and described herein, will become apparent to those skilled in the art. Such modifications are also intended to fall within the scope of the appended claims.

EXAMPLE 1

Continuous Production Of Sodium t-Butoxide As A 17% wt/wt Solution

A mixture of sodium metal (87.6 g, 3.81 mole) in 752 g of CYCLOSOL®53, a solvent consisting of a mixture of aromatic hydrocarbons manufactured by Shell Oil Company, Houston, Tex., in a 1.5 L double wall reactor with four baffles and a double 4-bladed skew propeller is blanketed with nitrogen and heated to 125° C. At 125°–130° C., the mixture is stirred rapidly to disperse the molten sodium metal and 5 g of a 1:1 mixture of t-butanol and CYCLOSOL®53 (2.5 g, 0.03 mole t-butanol) is added to initiate the reaction. The remaining t-butanol is added over a 3 hour period as a 1:1 mixture with CYLCOSOL®53 (277.3 g, 1.87 mole t-butanol) at 130° C. The resultant mixture is held at 130° C. with no stirring for 0.25 hours to separate the phases. A portion of the top phase (670.9 g) is separated by decantation to give a 17% wt/wt solution of sodium t-butoxide in CYCLOSOL®53. The remaining phase mixture consisting of a sodium t-butoxide solution in CYCLOSOL®53 (415.7 g) and molten sodium metal (44 g, 1.91 mole) is cooled to room temperature.

This cooled phase mixture is treated with a second mixture of fresh sodium metal (26.3 g, 1.14 mole) and 452 g of CYCLOSOL®53, blanketed with nitrogen and heated to 125° C. At 125°–130° C., the reaction mixture is stirred rapidly to disperse the molten sodium metal. The heated, stirred reaction mixture is treated with 169.6 g of a 1:1 mixture of t-butanol and CYCLOSOL®53 (1.14 mole t-butanol) over a 1.5 hour period at 125°–130° C. The resultant two phase mixture is held with no stirring at 130° C. for 0.25 hours. A 640.2 g portion of the top phase is separated by decantation to give a 17% wt/wt solution of sodium t-butoxide (1.13 mole sodium t-butoxide) in CYCLOSOL®53. The remaining phase mixture of 411.7 g of a solution of sodium t-butoxide in CYCLOSOL®53 and 44 g of molten sodium (1.91 mole) is cooled to room temperature.

The above procedure is then repeated to give a continuous production of sodium t-butoxide as a 17% wt/wt solution in CYCLOSOL®53.

EXAMPLE 2

Continuous Production Of Sodium t-Butoxide As A Solid

A mixture of sodium metal (77.3 kg, 3.36 kmole) in 668 kg of CYCLOSOL®53 in a reactor fitted with baffles and a propeller is blanketed with nitrogen and heated to 120°–130° C. The heated mixture is rapidly stirred to finely disperse the molten sodium metal and a 1:1 mixture of t-butanol and CYCLOSOL®53 (3.9 kg, 0.026 kmole of t-butanol) is added to initiate reaction. The remaining t-butanol is added as a 1:1 mixture with CYCLOSOL®53 (245.1 kg, 1.65 kmole of t-butanol) at 130° C. over a 1.5 hour period. The resultant two phase reaction mixture is held at 130° C. with no stirring for about 1 hour. A portion of the top phase (570 kg) is removed and cooled to about 20° C. The resultant white crystalline precipitate is filtered. The filtercake is washed with about 10 L of isohexane and dried at 30° C./400 mBar to give the title product as a white solid, 96 kg (1.0 kmole), 99–100% purity.

The mother liquor and isohexane washings containing sodium t-butoxide (0.65 kmole) in CYCLOSOL®53 are combined, recycled to the original reactor containing the remaining reaction phase mixture and heated to 135° C. to remove the isohexane. The resultant remaining reaction phase mixture is then included in a subsequent 1.0 kmolar reaction process as described hereinabove.

We claim:

1. A process for the manufacture of sodium $C_4$–$C_8$ alkoxide which comprises treating a stirred dispersion of sodium metal in a solvent under an inert atmosphere selected from the group consisting of nitrogen, helium and argon, with a less than stoichiometric amount of $C_4$–$C_8$ alkanol at a temperature of about 100° to 140° C. to form a mixture comprising a first phase and a second phase, wherein the first phase comprises a solution of the sodium $C_4$–$C_8$ alkoxide in the solvent and the second phase comprises the sodium metal, separating the first phase to obtain the product sodium $C_4$–$C_8$ alkoxide as the solution, and optionally continuously recycling the remaining mixture.

2. The process according to claim 1 wherein the solvent is an aromatic hydrocarbon or a mixture of aromatic hydrocarbons.

3. The process according to claim 1 wherein the inert atmosphere is nitrogen.

4. The process according to claim 1 wherein the amount of $C_4$–$C_8$ alkanol is about 0.10 to 0.90 molar equivalents.

5. The process according to claim 4 wherein the amount of $C_4$–$C_8$ alkanol is about 0.4 to 0.6 molar equivalents.

6. The process according to claim 1 wherein the remaining mixture is continuously recycled.

7. The process according to claim 1 wherein the temperature is about 120° to 130° C.

8. The process according to claim 1 wherein the $C_4$–$C_8$ alkanol is a tertiary $C_4$–$C_8$ alkanol.

9. The process according to claim 8 wherein the tertiary $C_4$–$C_8$ alkanol is t-butanol or t-amylalcohol.

10. The process according to claim 8 wherein the tertiary $C_4$–$C_8$ alkanol is t-butanol.

11. The process according to claim 5 wherein the $C_4$–$C_8$ alkanol is t-butanol and the temperature is 120°–130° C.

12. The process according to claim 1 wherein the first phase is cooled after separation and filtered to yield the sodium $C_4$–$C_8$ alkoxide as a solid.

13. A process for the manufacture of sodium $C_4$–$C_8$ alkoxide which comprises treating a stirred dispersion of sodium metal in a solvent optionally under an inert atmosphere with a less than stoichiometric amount of $C_4$–$C_8$ alkanol at a temperature of about 100° to 140° C. to form a mixture comprising a first phase and a second phase, wherein the first phase comprises a solution of the sodium $C_4$–$C_8$ alkoxide in the solvent and the second phase comprises the sodium metal, separating the first phase to obtain the product sodium $C_4$–$C_8$ alkoxide as the solution, and continuously recycling the remaining mixture.

14. The process according to claim 13 wherein the solvent is an aromatic hydrocarbon or a mixture of aromatic hydrocarbons.

15. The process according to claim 13 wherein the process is carried out under inert atmosphere.

16. The process according to claim 15 wherein the inert atmosphere is nitrogen.

17. The process according to claim 13 wherein the amount of $C_4$–$C_8$alkanol is about 0.10 to 0.90 molar equivalents.

18. The process according to claim 17 wherein the amount of $C_4$–$C_8$alkanol is about 0.4 to 0.6 molar equivalents.

19. The process according to claim 13 wherein the temperature is about 120° to 130° C.

20. The process according to claim 13 wherein the $C_4$–$C_8$alkanol is a tertiary $C_4$–$C_8$alkanol.

21. The process according to claim 20 wherein the tertiary $C_4$–$C_8$alkanol is t-butanol or t-amylalcohol.

22. The process according to claim 21 wherein the tertiary $C_4$–$C_8$alkanol is t-butanol.

23. The process according to claim 18 wherein the $C_4$–$C_8$alkanol is t-butanol and the temperature is 120°–130° C.

24. The process according to claim 13 wherein the first phase is cooled after separation and filtered to yield the sodium $C_4$–$C_8$alkoxide as a solid.

* * * * *